United States Patent [19]

NessAiver

[11] Patent Number: 5,329,925
[45] Date of Patent: Jul. 19, 1994

[54] REDUCED SCAN TIME CARDIAC GATED MAGNETIC RESONANCE CINE AND FLOW IMAGING

[75] Inventor: Moriel S. NessAiver, Cleveland Heights, Ohio

[73] Assignee: Picker International, Inc., Highland Hts., Ohio

[21] Appl. No.: 874,807

[22] Filed: Apr. 28, 1992

Related U.S. Application Data

[63] Continuation-in-part of Ser. No. 859,153, Mar. 27, 1992, which is a continuation-in-part of Ser. No. 791,855, Nov. 14, 1991, Pat. No. 5,273,040.

[51] Int. Cl.$^5$ .......................................... A61B 5/055
[52] U.S. Cl. ............................. 128/653.2; 128/653.3; 128/696; 324/306
[58] Field of Search ............... 128/653.2, 653.3, 696, 128/708; 324/306, 309

[56] References Cited

U.S. PATENT DOCUMENTS

| | | | |
|---|---|---|---|
| 4,570,119 | 2/1986 | Wehrli et al. | 324/306 |
| 4,683,431 | 7/1987 | Pattany et al. | 324/306 |
| 4,689,560 | 8/1987 | Nayler et al. | 324/306 |
| 4,710,717 | 12/1987 | Pelc et al. | 128/653.2 |
| 4,724,386 | 2/1988 | Haacke et al. | 324/309 |
| 4,767,991 | 8/1988 | Rzedzian | 128/653.2 |
| 4,885,537 | 12/1989 | Suzuki | 324/306 |
| 4,915,111 | 4/1990 | Sano et al. | 128/653.3 |
| 4,968,935 | 11/1990 | Ehman et al. | 324/306 |
| 5,031,624 | 7/1991 | Mistretta et al. | 128/653.3 |
| 5,042,485 | 8/1991 | Sano et al. | 128/653 |
| 5,151,656 | 9/1992 | Maier et al. | 324/309 |
| 5,167,232 | 12/1992 | Parker et al. | 128/653.2 |
| 5,273,040 | 12/1993 | Apicella et al. | 128/653.2 |

FOREIGN PATENT DOCUMENTS

| | | |
|---|---|---|
| 412819A2 | 2/1991 | European Pat. Off. . |
| 488496A2 | 6/1992 | European Pat. Off. . |
| 3514542 | 10/1986 | Fed. Rep. of Germany ... 128/653.2 |
| 3642083 | 7/1987 | Fed. Rep. of Germany ... 128/653.2 |
| 3835111 | 4/1989 | Fed. Rep. of Germany ... 128/653.2 |
| 3918625A1 | 12/1989 | Fed. Rep. of Germany . |

OTHER PUBLICATIONS

"Fast Antiography Using Selective Inversion Recovery", Wang, et al., Magnetic Resonance in Medicine, 23, 109–121 (1992).

(List continued on next page.)

*Primary Examiner*—K. M. Pfaffle
*Attorney, Agent, or Firm*—Fay, Sharpe, Beall, Fagan, Minnich & McKee

[57] ABSTRACT

A positive portion (52) of k-space and a negative portion (56) are both divided into n segments (FIG. 2 ). In each cardiac cycle, a multiplicity of field echoes (106) are generated, which multiplicity of gradient echoes are divided into groups of n contiguous echoes. Within each group, the echoes are all from either the positive portion of k-space or the negative portion of k-space. Preferably, every group of each cardiac cycle has the same views in the same order to generate like, time displaced frames of a cine image sequence. Within each group, the views from the central-most segment n are collected in the middle of the group, views from progressively less central, higher frequency segments are progressively less centrally located within each group with views of the most peripheral, highest frequency segments being collected at the ends of the group. The total number of segments is an integer multiple of four times the number of views per group to facilitate 0°–180° phase cycling. Quantitative flow images are generated by expanding each group to include corresponding views from the k-space for reference image data and a flow sensitized image data. The echo signals for the reference and flow sensitized images for each frame are separated and reconstructed into reference and flow sensitized images for each frame. The reference and flow sensitized images are subtracted to generate a quantitative flow image for each frame.

20 Claims, 8 Drawing Sheets

OTHER PUBLICATIONS

"Fast MR Cardiac Profiling with Two-Dimensional Selective Pulses" Cline, et al., Magnetic Resonance in Medicine, 17, 390–401 (1991).

"MR Fourier Transform Arteriography Using Spectral Decomposition" Cho, et al., Magnetic Resonance in Medicine, 16, 226–237 (1990).

"Extraction of Cardiac and Respiratory Motion Cycles by Use of Projection Data and Its Applications to NMR Imaging", Kim, et al., Magnetic Resonance in Medicine, 13, 25–37 (1990).

"Cineangiography of the Heart in a Single Breath Hold with a Segmented TubroFLASH Sequence", Atkinson, et al. Radiology 178:357–360; RSNA 1991.

"A Flow Velocity Zeugmatographic Interlace For NMR Imaging in Humans", Moran, Magnetic Resonance Imaging vol. 1, pp. 197–203 (1982).

"Measurement of Flow with NMR Imaging Using a Gradient Pulse and Phase Difference Technique", Bryant, et al. Journal of Computer Assisted Tomography, 8(4):588–593; Aug. 1984.

"Blood Flow: Magnetic Resonance Imaging", Bradley, et al. Radiology 1985 154:443–450.

REDUCED SCAN TIME CARDIAC GATED MAGNETIC RESONANCE CINE AND FLOW IMAGING

This application is a continuation-in-part of U.S. application Ser. No. 07/859,153, filed Mar. 27, 1992 which, in turn, is a continuation-in-part of U.S. application Ser. No. 07/791,855, now U.S. Pat. No. 5,273,040, filed Nov. 14, 1991.

BACKGROUND OF THE INVENTION

The present invention relates to the art of magnetic resonance cine imaging. It finds particular application in conjunction with quantitative flow cine imaging and will be described with particular reference thereto. It is to be appreciated, however, that the invention will also find application in conjunction with cardiac, angiography, circulatory, black blood cine, and other examinations in which flowing fluid is imaged.

Cine images have commonly been acquired using field echoes. Field echoes permit a rapid repetition rate, e.g. 64 sequence repetitions in 600 msec. In cardiac imaging, this enables a view of data for each of 64–100 frames or images to be collected in a single cardiac cycle. Each frame is displaced by about 10 milliseconds. When displayed sequentially, the frame images illustrate the cardiac cycle with a resolution of about 10 msec.

Generally, optimal cardiac gated cine images are achieved if all the views are collected within a single breath hold. Collecting all the views within a single breath hold eliminates the motion artifacts attributable to pulmonary motion. In the cardiac region, misrepresentation of heart position between breath holds can be significant.

A single breath hold is typically 16–20 heartbeats. Acquiring only one view per frame image in each cardiac cycle of a single breath hold would limit each frame image to 16–20 views. To increase the number of views per frame, data acquisition could be continued for several breath holds. However, the heart and surrounding tissue move with each pulmonary cycle and typically do not return accurately to the same position in subsequent breath holds.

One technique described in "Cineangiography of the Heart in a Single Breath Hold with a Segmented Turbo-FLASH Sequence", Radiology, Vol. 178, pp. 357–360, Atkinson and Edelman (RSNA, 1991), 128 lines or views of k-space were grouped into 8 segments of 16 views each. The resultant magnetic resonance echoes of each cardiac cycle were grouped into 16 groups of 8 views each. The number of groups are dependent on the patient's heart rate. The 8 views within each group of 16–20 consecutive heart beats were differently phase encoded and processed as 128 views (16×8) of the same frame image. In this manner, multiframe images of the cardiac cycle, each with 128 views per image, were generated. More specifically, in the first heart beat, views or lines 1, 17, 33, etc. were collected; in the second heart beat, lines 2, 18, 34, etc. were collected; and so forth. The raw data from these sets was combined or interleaved to form the 128 view data set for reconstruction into each of the multiple frames.

One of the drawbacks of the Atkinson and Edelman segmentation of k-space was that the resultant frames suffered from blurring. The present inventor has recognized that this blurring is attributable to the acquisition of the central views, the views with the most signal power and image information, at different times in subsequent cardiac cycles. In the above-illustrated 8 segment, 16 heart beat sequence, the central views in each group alternated between two different time displaced points in the cardiac cycle.

A common problem in magnetic resonance scanners is that eddy currents are generated in the cryostat by rapidly changing magnetic gradients, e.g. the phase encode gradients. These eddy currents cause a number of different image artifacts and distortions. Commonly, the effects of eddy currents are minimized by using sequences that have gradients of alternating polarity such that the eddy currents tend to cancel. One problem with the Atkinson technique is that it acquired views from both positive and negative k-space in a single heartbeat or repetition. If there is a rewind pulse, this resulted in two phase encode gradients of the same polarity being applied back-to-back. The back-to-back applications of two gradients of the same polarity tended to cause the gradient currents to add, rather than cancel, increasing gradient current artifacts and distortions.

In order to push DC artifacts and un-encoded signals from the center to the edge of an image, it is common to perform 0°–180° phase cycling of the RF. For example, the phase of the RF pulse is offset 180° in alternate views and cycles. With the Atkinson and Edelman technique, with some group and segment sizes, each group had both even and odd numbered views with even numbered views or odd numbered views back-to-back. This made 0°–180° phase cycling impossible.

In accordance with the present invention, a symmetric, centrally-ordered phase encode grouping of the views is provided which overcomes the above-referenced problems and others. The present invention further provides for a quantitative flow imaging technique which uses the symmetric, centrally-ordered phase encode grouping, as well as other segmentations of k-space.

SUMMARY OF THE INVENTION

In accordance with one aspect of the present invention, a cardiac gated series of field echo sequences is divided into groups in which positive and negative regions of k-space are treated separately.

In accordance with another aspect of the present invention, the views within each group are arranged such that the central most views (with the lowest frequency phase encoding) are generated at the same, generally central location within each group in subsequent cardiac cycles. More central views are generated on either side of the central-most view in each group or segment and the highest frequency views are generated at the ends of each group.

In accordance with another aspect of the present invention, the views within each group are centrally ordered to keep the acquisition of the central frequency views near the center of each group and the acquisition of the next lower frequency groups as close to the acquisition of the central frequency views as possible.

In accordance with a more limited aspect of the present invention, the positive half of k-space is divided into "n" segments of y/2 views each, where y equals the total number of views divided by the group size n. The first and last views in each group are taken from the highest frequency and next highest frequency segments of positive k-space. The second and next to last view in each group are taken from the third and fourth highest frequency segments. This sequence is repeated with views from progressively lower frequency segments of k-space with a view from the lowest frequency segment being located centrally within each group.

In accordance with another aspect of the present invention, the total number of views is a multiple of four times the total number of k-space segments. This facilitates 0°-180° phase cycling by enabling the views which are collected in each heartbeat to be all even or all odd.

In accordance with another aspect of the present invention, cardiac gated cine quantitative flow imaging is performed. During each cardiac cycle, views of both a reference image and a motion sensitized image are acquired and interleaved within a single heartbeat and a single breath hold.

In accordance with a more limited aspect of the present invention, the reference and motion sensitized views are interleaved within each group.

One advantage of the present invention is that it can be implemented on a standard MR scanner with no special hardware.

Another advantage of the present invention is that the resulting images have higher spatial resolution and higher signal to noise ratio than echo planar images.

Another advantage of the present invention is that all central views are acquired at the same point in each group, hence the same point in each cardiac cycle, which minimizes blurring.

Another advantage of the present invention is that it minimizes eddy current effects by treating positive k-space and negative k-space separately.

Yet another advantage of the present invention is that it enables the generation of quantitative flow cine images.

Still further advantages of the present invention will become apparent to those of ordinary skill in the art upon reading and understanding the following detailed description of the preferred embodiments.

BRIEF DESCRIPTION OF THE DRAWINGS

The invention may take form in various components and arrangements of components, and in various steps and arrangements of steps. The drawings are only for purposes of illustrating a preferred embodiment and are not to be construed as limiting the invention.

DETAILED DESCRIPTION OF THE PREFERRED EMBODIMENTS

Figure 1A:
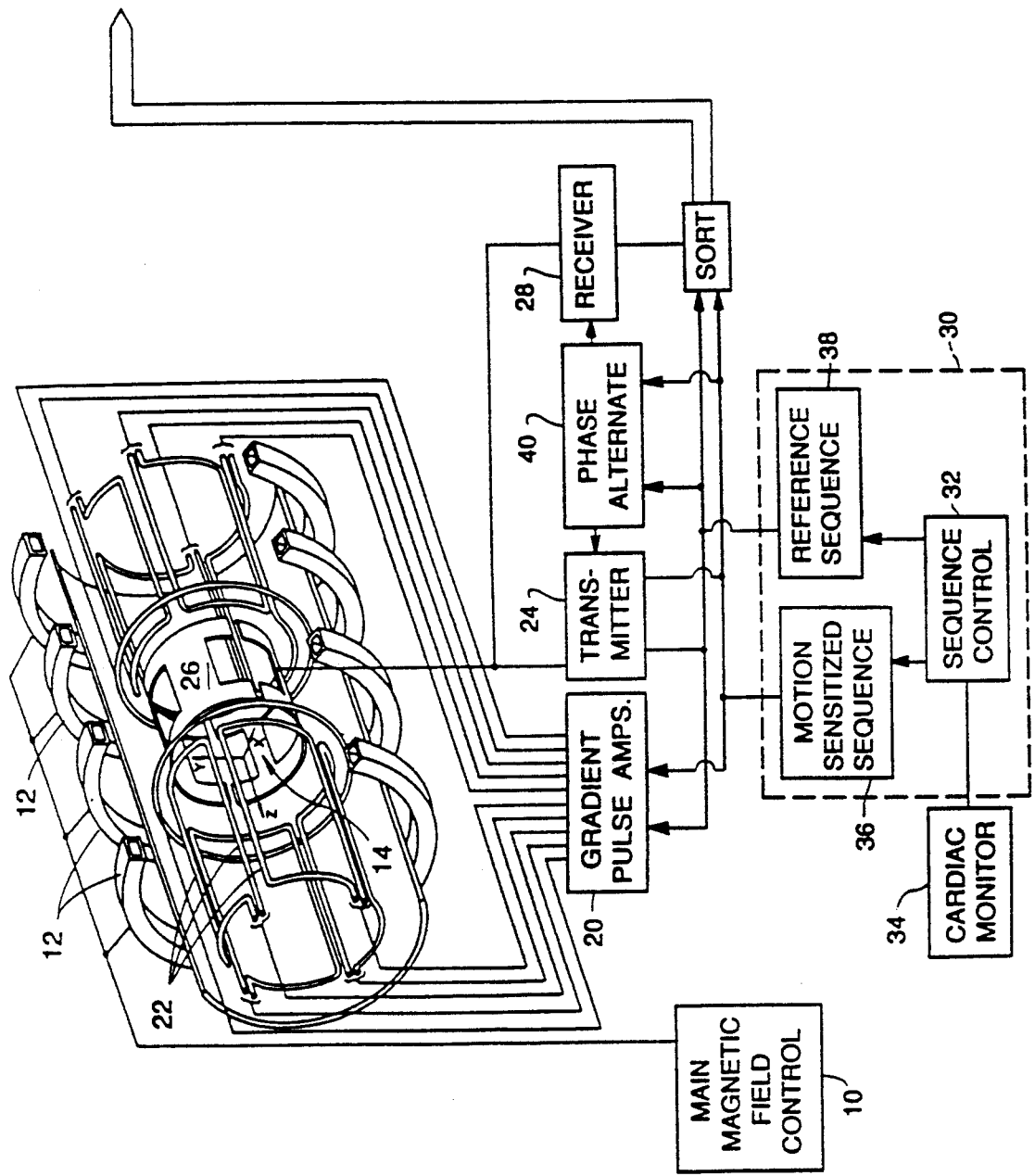
FIGS. 1A and 1B taken together are a diagrammatic illustration of a magnetic resonance imaging system in accordance with the present invention.
Figure 1B:
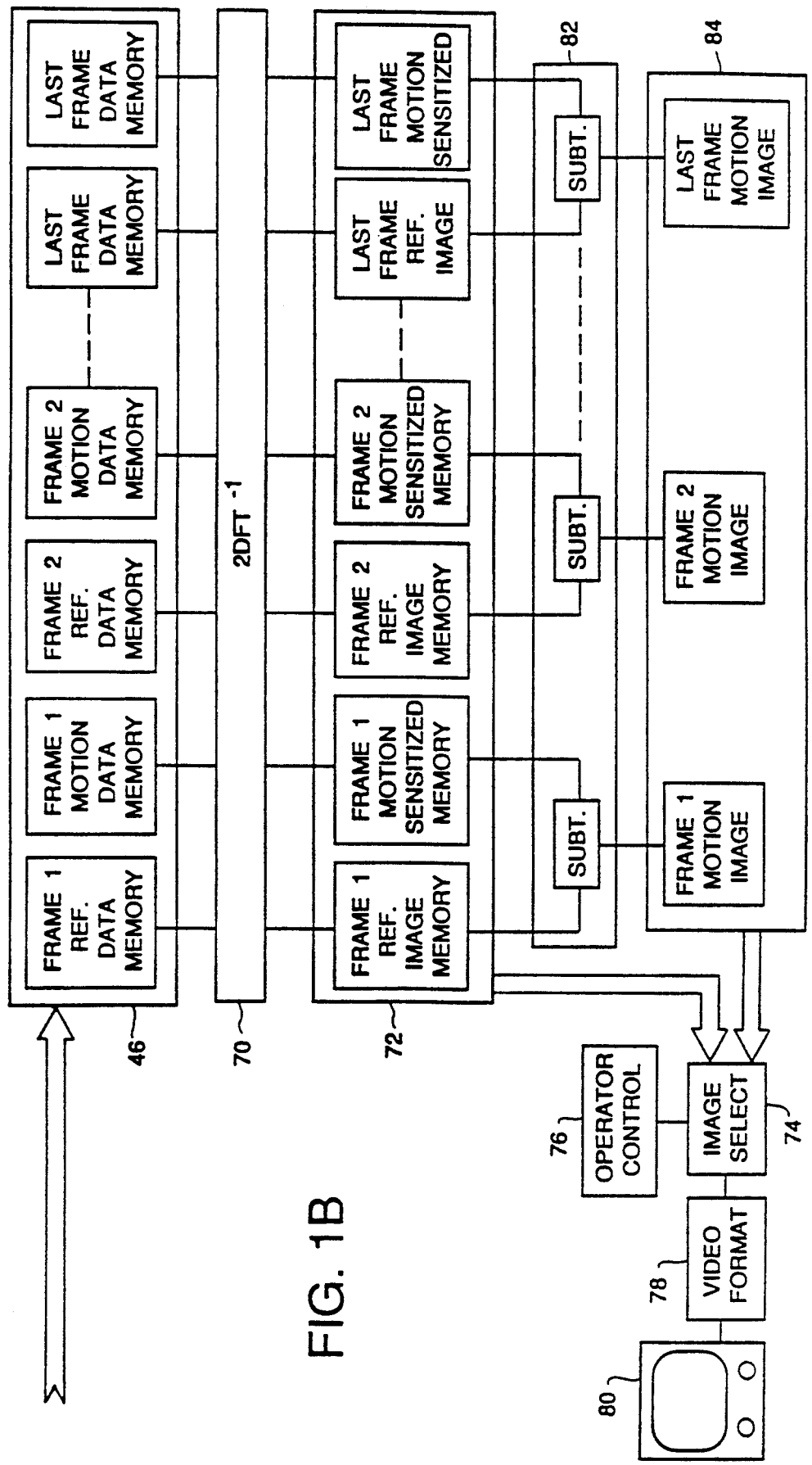

With reference to FIGS. 1A and 1B, a main magnetic field control means 10 controls superconducting or resistive magnets 12 such that a substantially uniform main magnetic field is created longitudinally along a z-axis through an examination region 14. A magnetic resonance echo generating means applies sequences of RF and magnetic field pulses to cause magnetic resonance echoes, preferably field or gradient echoes, to be generated. More specifically, gradient pulse amplifiers 20 apply current pulses to gradient coils 22 to create gradient magnetic fields along orthogonal x, y, and z-axes of the examination region. A radio frequency transmitter 24 transmits RF pulses to an RF coil 26 to transmit RF pulses into the examination to excite magnetic resonance and manipulate excited magnetic resonance. A radio frequency receiver 28 receives magnetic resonance signals emanating from the examination region that are picked up by the RF coil 26 or by surface coils (not shown).

A sequence control means 30 controls the gradient pulse amplifiers 20 and the transmitter 24 to generate a series of field or gradient echo imaging sequences. More specifically to the preferred embodiment, a master sequence control 32 is gated by a cardiac monitor 34 to start a series of field echo sequences. The master sequence control means 32 controls a motion sensitized sequence control 36 and a reference or motion insensitive sequence control 38. The motion sensitive and reference sequence controls implement analogous field echo imaging sequences such as sequences in which the gradients along one of the axes are time or amplitude shifted relative to the other, such as shown for example, in U.S. Pat. No. 4,689,560 of Nayler and Pattany.

A polarity alternating means 40 causes 0°-180° cycling of the RF. In the preferred embodiment, the phase alternating means includes a means 40 which causes the phase of the radio frequency excitation pulse and the receiver 28, preferably a digital receiver, to be reversed in alternate views.

Figure 2:
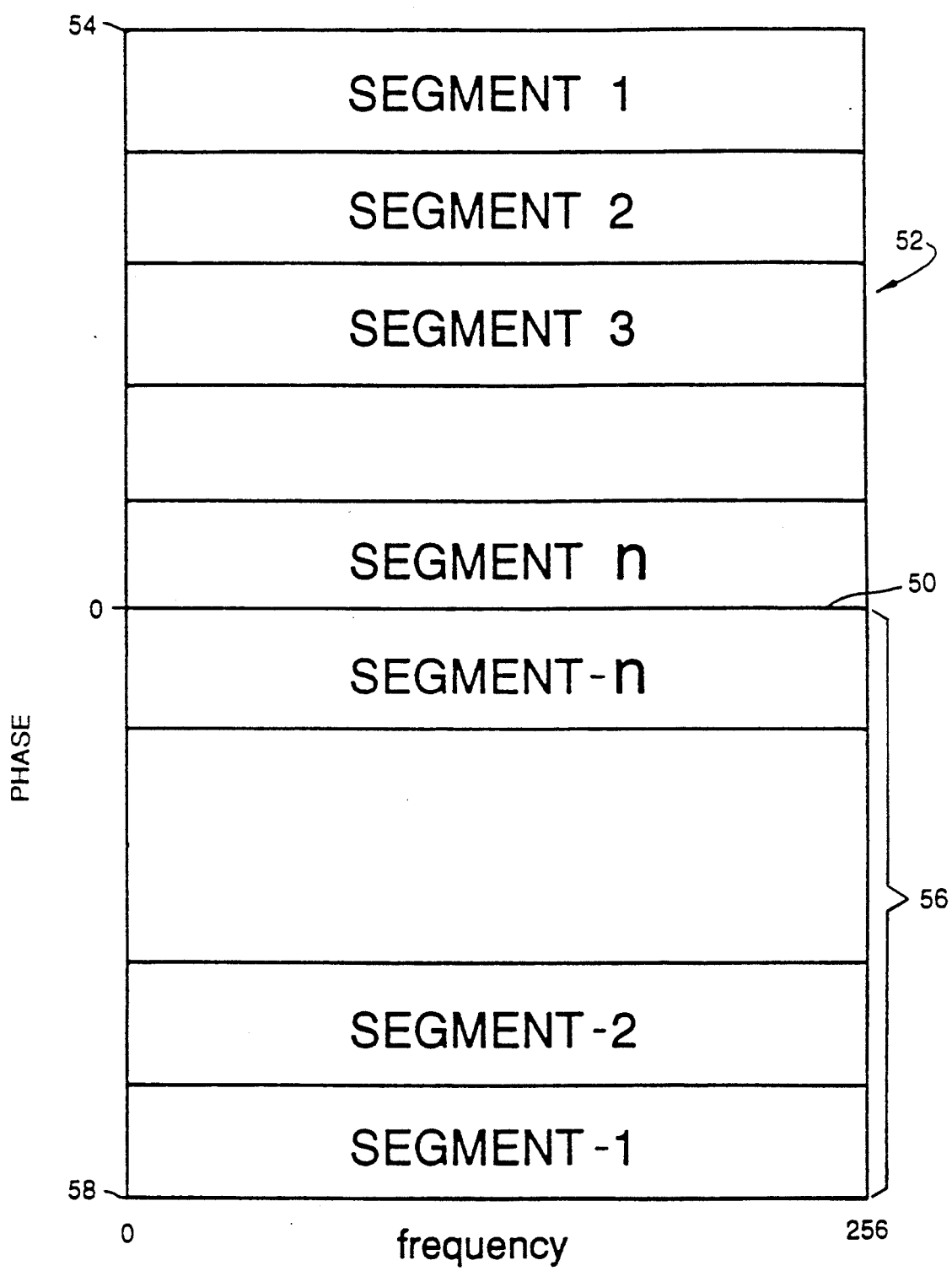
FIG. 2 illustrates a preferred segmentation of k-space.
Figure 3:
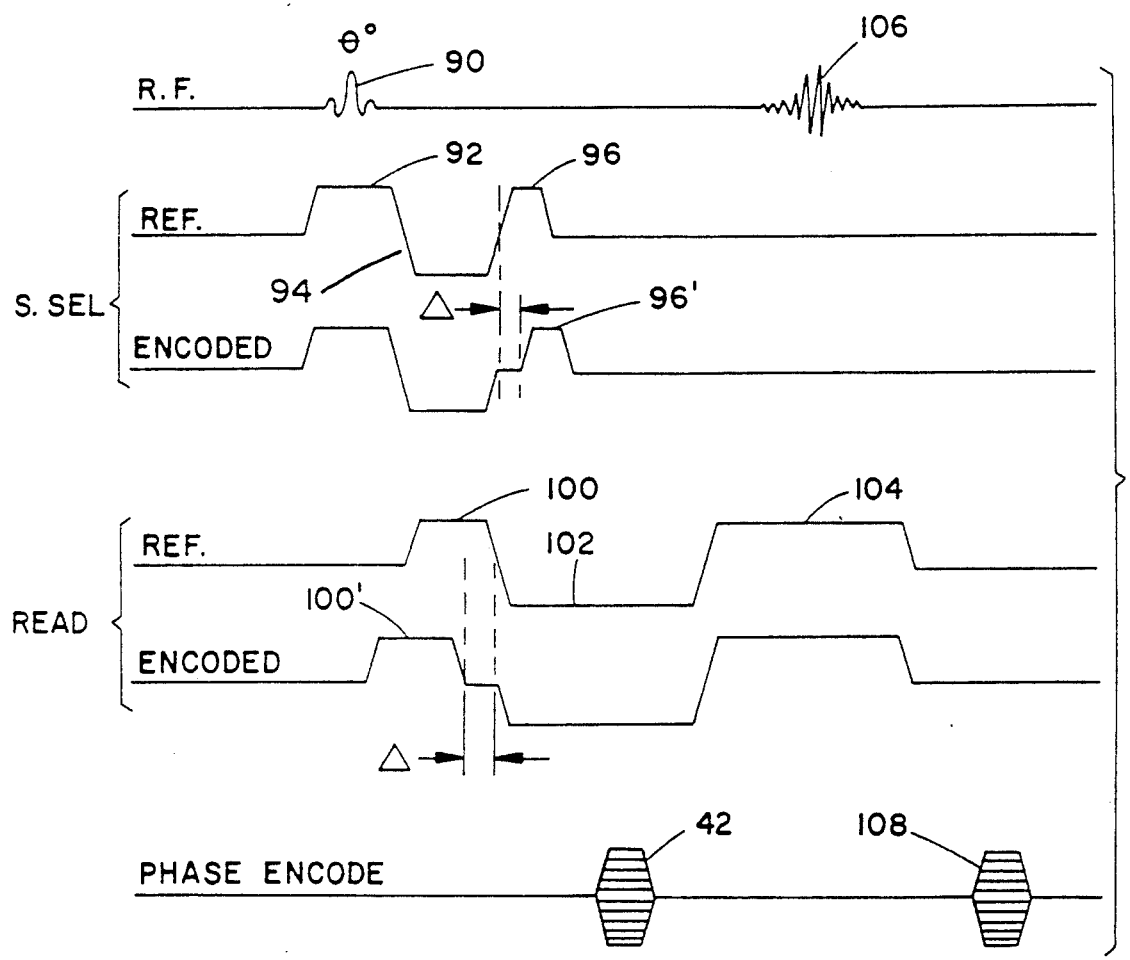
FIG. 3 illustrates exemplary motion sensitized and reference magnetic resonance sequences.

With reference to FIG. 2, each magnetic resonance echo signal received by the receiver 28 corresponds to one view or line of data for a corresponding one of the frames of the cine image sequence. Each view includes a plurality, e.g. 256 frequency encoded digital values. Each view is phase encoded with one of 2n of phase encodings. That is, in each repetition of the field echo sequence, such as illustrated in FIG. 3, a phase encode gradient 42 is applied with one of n positive (or zero) or one of n negative steps. A sorting means 44 (FIG. 1A) sorts the echo signals corresponding to the same frame of the cine image among a plurality of frame image memories 46 (FIG. 1B).

As shown in FIG. 2, the data in each of memories 46 is stored as a matrix of data which is phase encoded in one direction and frequency coded in another, commonly known as k-space. A central phase encoded view 50 has zero phase encoding. Each view on a positive side 52 of k-space has progressively an additional step of phase encoding up to a top view 54 which has the most or highest frequency phase encoding. Analogously, the views phase encoded with an opposite polarity are in a negative portion 56 of k-space. Each view in the negative portion of k-space has progressively one step greater phase encoding of an opposite polarity up to a bottom view 58 which has a maximum or highest frequency negative polarity phase encoding. The views closest to the central or zero phase encoding view 50 carry the most image information and the best signal to noise ratio.

Figure 4:
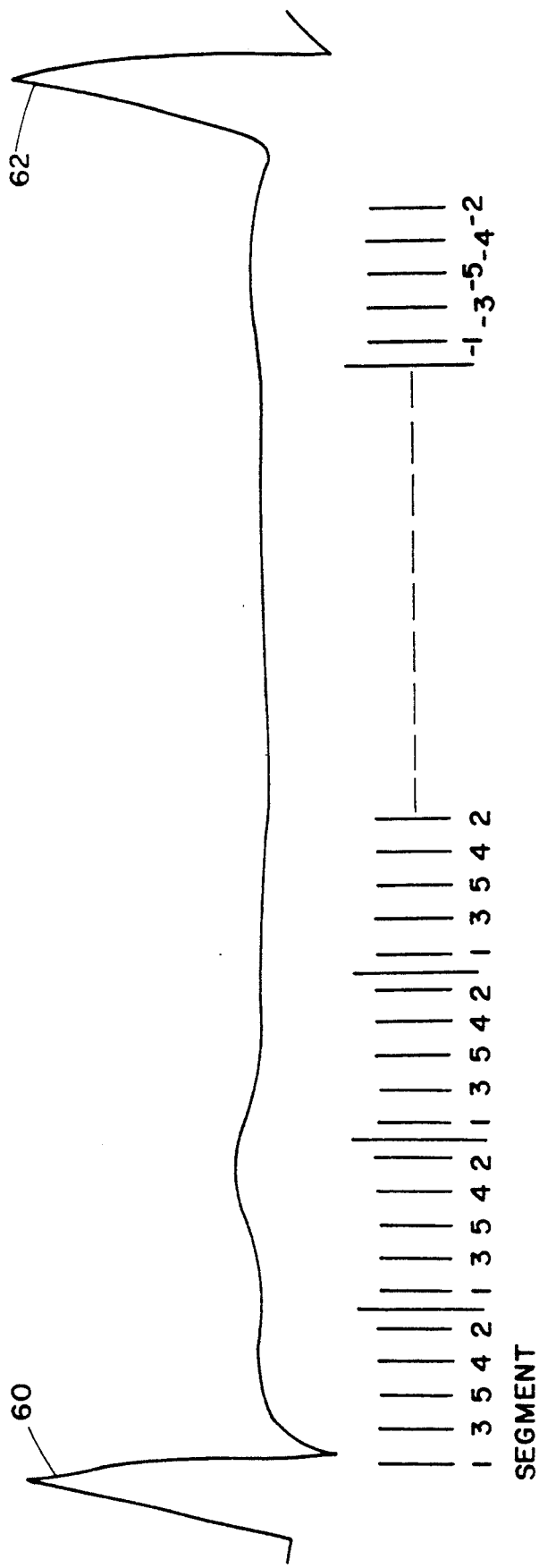
FIG. 4 depicts a heartbeat of a cardiac gated cine acquisition in relative time sequence with grouped views in accordance with a preferred embodiment of the present invention.

With reference to FIG. 4 and continuing reference to FIG. 2, an earlier cardiac cycle 60 causes the cardiac monitor 34 to trigger a series of field echo sequences, e.g. 64 or more sequences with about a 10 msec. repeat time. The 64 repetitions of the gradient echo sequence occur in the interval before a subsequent R-wave 62, i.e. spanning a single cardiac cycle. The k-space is then divided into 2n segments with segments n and −n being most central and segments 1 and −1 being most peripheral, i.e. having the highest frequency components. Analogously, the repetitions of the field echo sequence within each heart beat are divided into groups of n views. Each segment of k-space has y/2 views, where y is the number of imaged cardiac cycles within a single breath hold.

The generated magnetic resonance echoes are analogously divided into groups of n contiguous echoes or views. Views from the nth or central-most k-space segment occur at the same, central location within each group. In the example illustrated FIG. 4 in which n=5, the central-most echo of each group comes from the fifth segment. The two views most closely adjoining the central-most view come from the next two lowest segments, i.e. the third and fourth segments of k-space. The next most central views are arranged next, and so on, until the views from the least central segments which are located at the ends of each group. Table 1 illustrates the order of the segments from which the views come within each group for group sizes between 3 and n.

TABLE 1

| Group Size | Segment Order Number |
|---|---|
| 3 | 1, 3, 2 |
| 4 | 1, 3, 4, 2 |
| 5 | 1, 3, 5, 4, 2 |
| 6 | 1, 3, 5, 6, 4, 2 |
| 7 | 1, 3, 5, 7, 6, 4, 2 |
| 8 | 1, 3, 5, 7, 8, 6, 4, 2 |
| 9 | 1, 3, 5, 7, 9, 8, 6, 4, 2 |
| n (odd) | 1, 3, 5, . . . , (n-2), n, (n-1), . . . , 6, 4, 2 |
| n (even) | 1, 3, 5, . . . , (n-1), n, (n-2), . . . , 6, 4, 2 |

After collecting the positive k-space data, the series of sequences is repeated for the views of the negative half of k-space. The views from the corresponding negative segments occur at the same relative location within each group, i.e. at the same time in the cardiac cycle.

Figure 5:
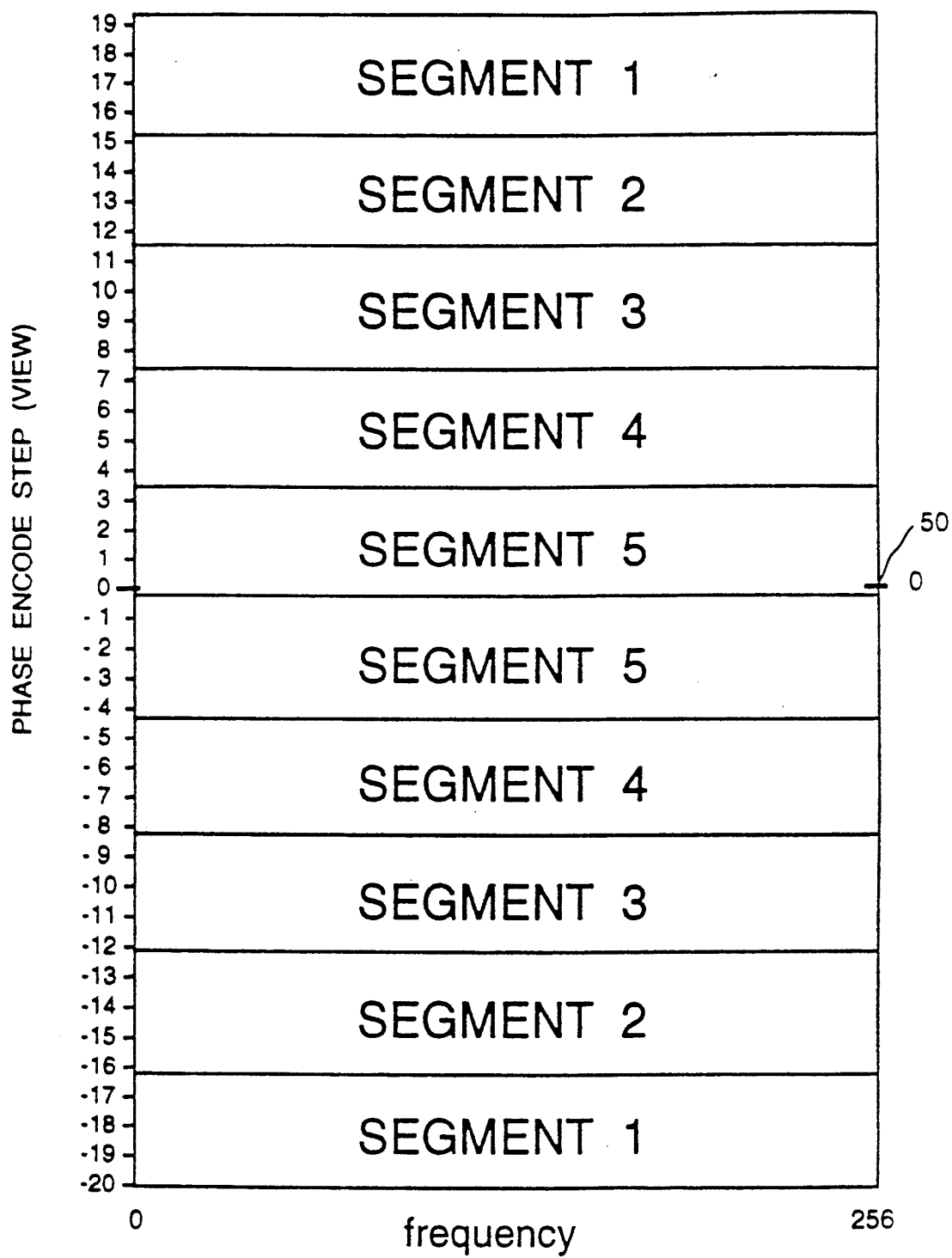
FIG. 5 illustrates a 5-way symmetric, centrally-ordered segmentation of k-space with a 40 view imaging sequence.
Figure 6:
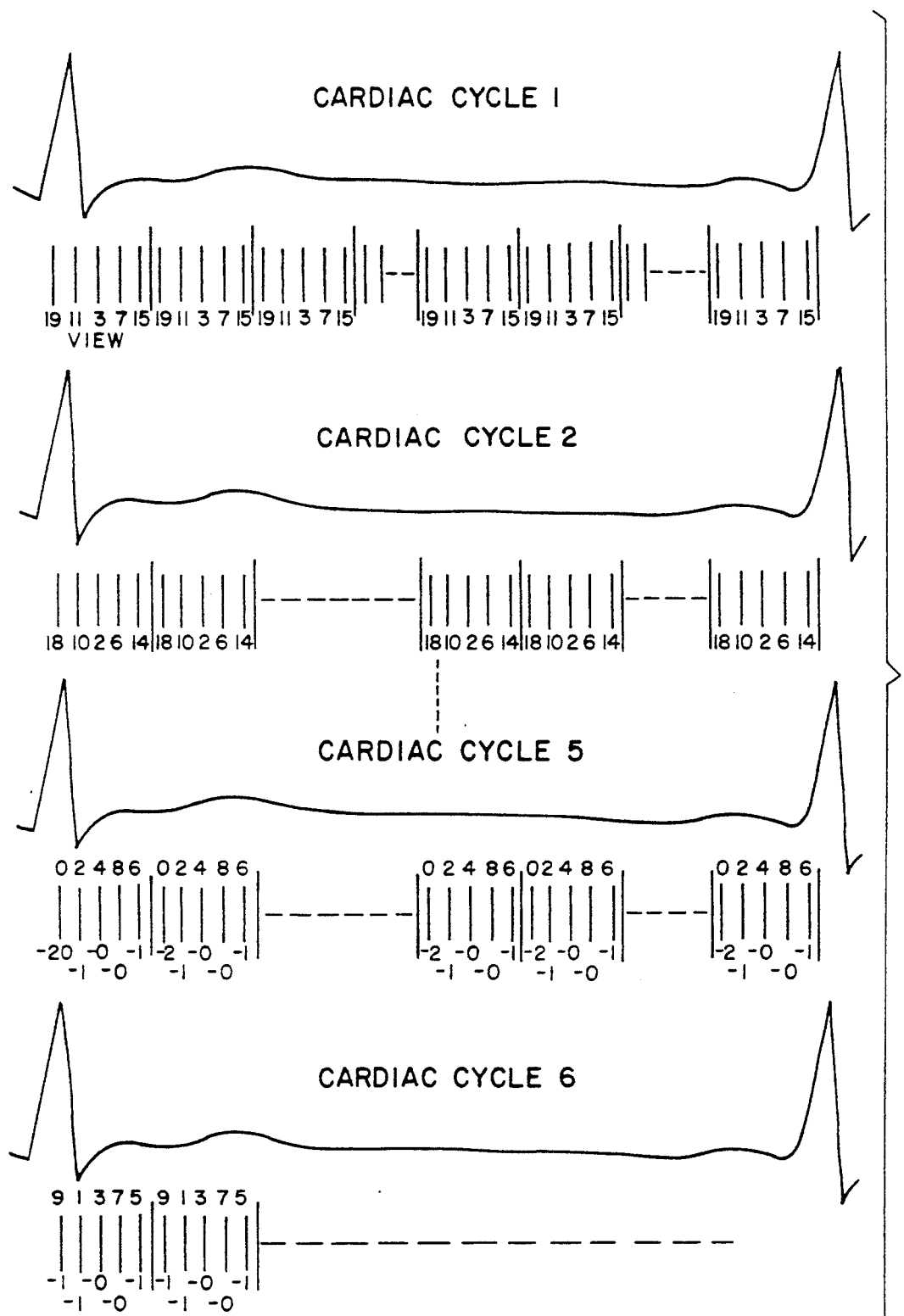
FIG. 6 illustrates the views collected in each of several cardiac cycles.

When the total number of views collected is an integer multiple of 2 (but not an integer multiple of 4), then, even and odd views can occur back-to-back, interfering with 0°–180° phase cycling. In order to provide for 0°–180° phase cycling, the number of views is preferably a multiple of 4 times the group size. FIGS. 5 and 6 give an example in which the number of segments is 5 and the total number of views is 40. As illustrated in FIG. 5, the central-most view 50 is denoted as the 0th view. The nth or 5th segment on the positive side of k-space includes views 0 through 3, the fourth segment includes views 4 through 7, . . . , and the first segment includes views 16 through 19. Analogously, in the negative half of k-space, the nth or 5th segment includes views −1 through −4, the fourth segment includes views −5 through −8, . . . , and the first segment includes views −17 through −20. In this manner, k-space includes 40 views which are divided into 5 segments which enables the entirety of k-space to be sampled in eight cardiac cycles. Only even numbered views in the positive half of k-space are sampled in a given cardiac cycle, only odd numbered views in the positive half of k-space are sampled in a given cardiac cycle, only odd views in negative k-space are sampled in a given cardiac cycle, and only even views in the negative half of k-space are sampled in a given cycle. As illustrated in FIG. 6, in a first cardiac cycle, the views of k-space are sampled in the order 19, 11, 3, 7, 15. In the second cardiac cycle, the views are sampled in the order 18, 10, 2, 6, 14. In the third and fourth cardiac cycles, the rest of positive k-space is sampled. In the fifth cardiac cycle, the views are sampled −17, −9, −1, −5, −13. In a sixth cardiac cycle, the views are sampled −18, −10, −2, −6, −14. The rest of negative k-space is sampled in the seventh and eighth cardiac cycles. The complete collection of all 40 views in this example is summarized in Table 2 below.

TABLE 2

| Cardiac Cycle | Views in Each Group | | | | |
|---|---|---|---|---|---|
| 1 | 19, | 11, | 3, | 7, | 15 |
| 2 | 18, | 10, | 2, | 6, | 14 |
| 3 | 17, | 9, | 1, | 5, | 13 |
| 4 | 16, | 8, | 0, | 4, | 12 |
| 5 | −17, | −9, | −1, | −5, | −13 |
| 6 | −18, | −10, | −2, | −6, | −14 |
| 7 | −19, | −11, | −3, | −7, | −15 |
| 8 | −20, | −12, | −4, | −8, | −16 |

Returning again to FIGS. 1A and 1B, the sorting means 44 sorts the views corresponding to each frame into a corresponding one of the frame memories 46. The views are sorted to create a k-space matrix essentially as shown in FIG. 5, for the example of five views per group. A two-dimensional inverse Fourier transform or other image reconstruction means 70 reconstructs each matrix into a corresponding image representation which is stored in a corresponding frame image memory 72. An image selecting means 74 is controlled by an operator control panel 76 or the like to select one or more of the frame images for display. A video formatting means 78 adjusts the format of each selected image into an appropriate format for display on a video monitor 80. Preferably, the operator can control the image selecting means to select each frame image in order at a selectable rate such that the display on the video monitor illustrates the movement of the heart during the cardiac cycle.

This same technique can be utilized to generate quantitative flow images. Within a single breath hold, and preferably within a single cardiac cycle, the gradient echo sequences are applied to generate field echoes corresponding to views of a motion sensitive image and a reference image. The views of a reference image for each frame are sorted by the sorting means and stored in a frame reference memory for each imaged frame. Analogously, the views of a motion sensitized frame are sorted by frame into corresponding ones of frame memories 46. The reference and motion sensitized views are reconstructed frame by frame to construct reference and motion sensitized images for each of the frames by the reconstruction means 70. A subtracting means 82 subtracts the reference and motion sensitized images corresponding to each frame to create a difference or quantized motion image which is stored in corresponding quantized motion image memories 84. The image selecting means 74 is connected with the quantized motion image memory 84 such that a cine sequence of quantized motion images is displayable on the video monitor 80.

With reference to FIG. 3, both the reference and motion sensitive sequences are initiated by the simultaneous application of an RF pulse 90 and a slice select gradient 92 of a first polarity. A complimentary slice select pulse 94 of the opposite polarity and a third slice select pulse 96 of the first polarity follow. For simplicity of illustration, the three slice select pulses are of identical amplitudes with durations such that the pulse 96 is half the duration of pulse 94 and approximately matches the section of pulse 92 which occurs after the center of the RF excitation pulse 90. The magnitudes and duration of the pulses in the slice select direction are selected such that the magnetization of material moving perpendicular to the slice plane is rephased. In an orthogonal direction, a read gradient pulse 100 of one polarity is followed by a second read gradient pulse 102 of an opposite polarity, followed by a read gradient 104 which frequency encodes a resultant field or gradient echo 106. For simplicity of illustration, the read gradient pulses 100, 102, and 104 are illustrated as being of identical amplitude with the pulse 100 being about half the duration of pulse 102 and approximately matching the duration between the initiation of gradient pulse 104 and the center of the resultant echo of 106. The magnitudes and duration of the slice selection pulses are selected such that the magnetization of material moving parallel to the read axis is rephased. The phase encode gradient 42 is applied before the gradient echo 106 with one of the phase encode gradient steps or views of k-space as described, for example in FIG. 5. Following the echo, an unwind phase gradient 108 is applied with the opposite polarity to the phase encode gradient 42 to remove the phase encoding from the system. This prevents the phase encoding from being carried forward into the next repetition of the sequence.

The gradient pulse in the direction of the flow component which is to be phase mapped is altered to encode flow into the gradient echo. In the illustrated embodiment, in the motion sensitized imaging sequence, the slice select gradient component 96' is shifted an amount Δ relative to gradient component 96 in the reference sequence. Analogously, in the motion sensitized sequence read gradient component 100' may be shifted relative to reference sequence gradient component 100 to encode the flow component in the read direction. To read the flow component oblique to both the slice select and read directions, slice select and read gradient components are both shifted. Alternately, the gradient pulses may be amplitude shifted or otherwise altered as explained in greater detail in U.S. Pat. No. 4,689,560.

To encode velocity the gradient pulses are amplitude and time scaled such that the 0th moment between the center of the excitation pulse 90 and the field echo 106 are zeroed, but such that the first moment changes between the reference and motion sensitive sequences. Preferably, second and higher order moments are also zeroed in both. In this manner, the difference represents the first moment or velocity. Analogously, by zeroing the first and second moments but not the second, acceleration can be imaged. Analogously, by creating a non-zero 0th moment, the static material is imaged. In some instances, it may be advantageous to display an image of the static material at half intensity or in black and white concurrently with a superimposed color display of flow velocity to improve the viewer's spatial reference.

First, the motion encoded and reference images can be collected in two separate scans in two breath holds. This maximizes the number of frame images available, but creates the possibility of mis-registration between the flow encoded and reference images. Second, the reference and motion sensitized images may be acquired in alternate cardiac cycles of the same breath hold. This is advantageous because the reference and motion sensitized scans occur at the same point in the cardiac cycle, but this is difficult to implement on many commercially available scanners. Third, the reference and motion sensitized groups of views may be alternated or interleaved within a single cardiac cycle and the full set of data collected in a single breath hold. However, this results in a time mis-registration between the corresponding reference and motion sensitized views. This mis-registration is about a 13 msec. times the number of views per group, i.e. about 65 msec. for groups of five. Fourth and preferred, the corresponding views of the reference and motion sensitized images are interleaved within each group.

Figure 7:
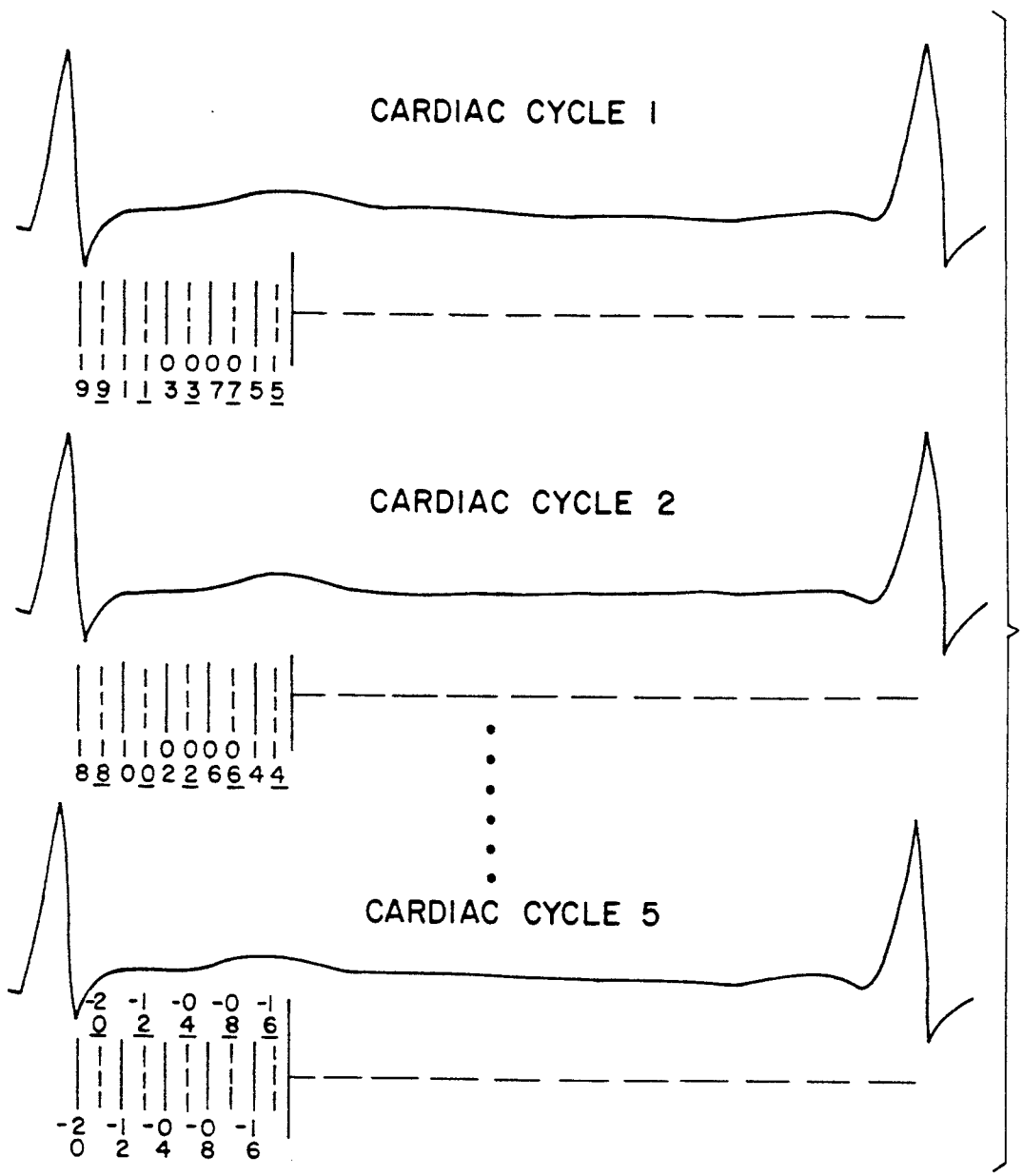
FIG. 7 illustrates an interleaved grouping of motion sensitized and reference views within each group in accordance with the present invention.

With reference to FIG. 7, in which the five view grouping example is again continued, each group now has five reference views from segments 1-5 (not underlined) and the corresponding five motion sensitized views from segments 1-5 (underlined), expanding each group to ten views. This, of course, reduces the number of frames by half. The entire sequence is illustrated in Table 3 below where underlined views are motion sensitized and nonunderlined views are reference views.

TABLE 3

| Cardiac Cycle | Views in Each Group | | | | | | | | |
|---|---|---|---|---|---|---|---|---|---|
| 1 | 19, | _19,_ | 11, | _11,_ | 3, | _3,_ | 7, | _3,_ | 15, | _15_ |
| 2 | 18, | _18,_ | 10, | _10,_ | 2, | _2,_ | 6, | _6,_ | 14, | _14_ |
| 3 | 17, | _17,_ | 9, | _9,_ | 1, | _1,_ | 5, | _5,_ | 13, | _13_ |
| 4 | 16, | _−16,_ | 8, | _8,_ | 0, | _0,_ | 4, | _4,_ | 12, | _12_ |
| 5 | −17, | _−17,_ | −9, | _−9,_ | −1, | _−1,_ | −5, | _−5,_ | −13, | _−13_ |
| 6 | −18, | _−18,_ | −10, | _−10,_ | −2, | _−2,_ | −6, | _−6,_ | −14, | _−14_ |
| 7 | −19, | _−19,_ | −11, | _−11,_ | −3, | _−3,_ | −7, | _−7,_ | −15, | _−15_ |
| 8 | −20, | _−20,_ | −12, | _−12,_ | −4, | _−4,_ | −8, | _−8,_ | −16, | _−16_ |

TABLE 3-continued

| Cardiac Cycle | Views in Each Group |
|---|---|

In this manner, corresponding reference and motion sensitized views are time offset by only a single gradient echo sequence repetition time, about 13 msec. in the preferred embodiment.

Although illustrated in conjunction with the central weighting of the low frequency phase encode data, it is to be appreciated that this quantitative motion imaging technique is also applicable to techniques that are not centrally ordered, such as in the 40 view k-space example illustrated in Table 4 below.

TABLE 4

| Cardiac Cycle | Views in Each Group |||||||||
|---|---|---|---|---|---|---|---|---|---|
| 1 | 0,  | 0,  | 4,  | 4,  | 8,  | 8,  | 12, | −12, | 16, | −16 |
| 2 | −1, | −1, | −5, | −5, | −9  | −9, | −13,| −13, | −17,| 14 |
| 3 | 1,  | 1,  | 5,  | 5,  | 9,  | 9,  | 13, | 13,  | 17, | 17 |
| 4 | −2, | −2, | −6, | −6, | −10,| −10,| −14,| −14, | −18,| 18 |
| 5 | 2,  | 2,  | 6,  | 6,  | 10, | 10, | 14, | 14,  | 18, | 18 |
| 6 | "3, | −3, | −7, | −7, | −11,| −11,| −15,| −15, | −19,| −19 |
| 7 | 3,  | 3,  | 7,  | 3,  | 11, | 11, | 15, | 15,  | 19, | 19 |
| 8 | −4, | −4, | −8, | −8, | −12,| −12,| −16,| −16, | −20,| −20 |

Other echo sequences for flow and static imaging are also contemplated such as the sequence of parent application Ser. No. 07/859,153, prior U.S. Pat. Nos. 4,689,560 and 4,683,431, and prior art articles "Blood Flow: Magnetic Resonance Imaging" Bradley, et al. (RSNA 1985); "A Flow Velocity Zeugmatographic Interlace for NMR Imaging in Humans", Moran, Magnetic Resonance Imaging, Vol. 1, pp. 197–203 (1982); and "Measurement of Flow with NMR Imaging Using a Gradient Pulse and Phase Difference Technique", Bryant, et al., J. Comp. Asst. Tomography 8(4):588–593 (1984), the disclosures of which are incorporated herein by reference.

The invention has been described with reference to the preferred embodiment. Obviously, modifications and alterations will occur to others upon reading and understanding the preceding detailed description. It is intended that the invention be construed as including all such modifications and alterations insofar as they come within the scope of the appended claims or the equivalents thereof.

Having thus described the preferred embodiment, the invention is now claimed to be:

1. A cine magnetic resonance imaging method comprising:
   (a) monitoring cardiac cycles of a subject in a magnetic resonance imaging region;
   (b) in coordination with each monitored cardiac cycle, generating a series of groups of consecutive echo sequences and receiving a corresponding plurality of echo signals, each echo signal corresponding to one view of k-space, a positive portion of k-space being segmented into n segments, a negative portion of k-space being segmented into a corresponding n segments, all of the views of each group being from one of the positive k-space portion and the negative k-space portion;
   (c) repeating step (b) with each of the groups at substantially the same time in each of a plurality of the monitored cardiac cycles;
   (d) sorting the echo signals by group such that each group corresponds to a different time interval of each of the subject's cardiac cycles;
   (e) reconstructing a frame image representation from the echo signals of each group.

2. The method as set forth in claim 1 wherein
   the echo sequence generating step includes generating a motion sensitized echo sequence and a reference echo sequence and receiving a motion sensitized echo signal and a reference echo signal corresponding to each view of k-space;
   in the sorting step, the reference and motion sensitized echo signals corresponding to each frame are separated;
   in the reconstructing step, the motion sensitized and reference echo signals of each group are reconstructed into separate reference and motion sensitized frame images; and
   further including subtracting the reference and motion sensitized frame images corresponding to the same group to create a flow image, whereby a plurality of flow images each corresponding to one of the time intervals of the subject's cardiac cycle are generated.

3. The method as set forth in claim 2 wherein in each group, corresponding reference and motion sensitive views are collected back-to-back in the same group.

4. A cine magnetic resonance imaging method in which a positive portion of k-space is segmented into n segments and a negative portion of k-space is segmented into a corresponding n segments, the first segment of both positive and negative k-space containing views with highest order frequency components, subsequent segments containing views with progressively lower order frequency components, and nth positive and negative segments containing views with central-most, lowest order frequency components, the method comprising:

(a) monitoring cardiac cycles of a subject in a magnetic resonance imaging region;

(b) in coordination with each monitored cardiac cycle, generating a series of groups of consecutive echo sequences and receiving a corresponding plurality of echo signals, each echo signal corresponding to one view of k-space, all of the views in each group being from one of the positive k-space portion and the negative k-space portion, echo signals corresponding to views from the nth positive and negative segments of k-space are generated most central within each group and echo signals corresponding to views from the first and second segmentations of k-space are at the ends of each group, whereby the central views are collected in the middle of each time interval of the subject's cardiac cycle;

(c) repeating step (b) with each of the groups at substantially the same time in each of a plurality of the monitored cardiac cycles;

(d) sorting the echo signals by group such that each group corresponds to a different time interval of each of the subject's cardiac cycles;

(e) reconstructing a frame image representation from the echo signals of each group.

5. The method as set forth in claim 4 wherein the views in k-space are numbered sequentially and wherein in each group, all of the views are one of even and odd numbered views.

6. The method as set forth in claim 5 wherein
the echo sequence generating step includes generating a motion sensitized echo sequence and a reference echo sequence and receiving a motion sensitized echo signal and a reference echo signal corresponding to each view of k-space;

in the sorting step, the reference and motion sensitized echo signals corresponding to each frame are separated;

in the reconstructing step, the motion sensitized and reference echo signals of each group are reconstructed into separate reference and motion sensitized frame images; and further including subtracting the reference and motion sensitized frame images corresponding to the same group to create a flow image, whereby a plurality of flow images each corresponding to one of the time intervals of the subject's cardiac cycle are generated.

7. The method as set forth in claim 6 wherein in each group, corresponding reference and motion sensitive views are collected back-to-back in the same group.

8. The method as set forth in claim 4 wherein
the echo sequence generating step includes generating a motion sensitized echo sequence and a reference echo sequence and receiving a motion sensitized echo signal and a reference echo signal corresponding to each view of k-space;

in the sorting step, the reference and motion sensitized echo signals corresponding to each frame are separated;

in the reconstructing step, the motion sensitized and reference echo signals of each group are reconstructed into separate reference and motion sensitized frame images; and further including subtracting the reference and motion sensitized frame images corresponding to the same group to create a flow image, whereby a plurality of flow images each corresponding to one of the time intervals of the subject's cardiac cycle are generated.

9. The method as set forth in claim 8 wherein in each group, corresponding reference and motion sensitive views are collected back-to-back in the same group.

10. A cine magnetic resonance imaging method in which a positive portion of k-space is segmented into n segments and a negative portion of k-space is segmented into a corresponding n segments, the first segment of both positive and negative k-space containing views with highest order frequency components, subsequent segments containing views with progressively lower order frequency components, and nth positive and negative segments containing views with central-most, lowest order frequency components, the method comprising:

(a) monitoring cardiac cycles of a subject in a magnetic resonance imaging region;

(b) in coordination with each monitored cardiac cycle, generating a series of groups of consecutive echo sequences and receiving a corresponding plurality of echo signals, each echo signal corresponding to one view of k-space, the views in k-space being numbered sequentially, all of the views in each group being from one of the positive k-space portion and the negative k-space portion, all of the views are one of even and odd numbered views;

(c) repeating step (b) with each of the groups at substantially the same time in each of a plurality of the monitored cardiac cycles;

(d) sorting the echo signals by group such that each group corresponds to a different time interval of each of the subject's cardiac cycles;

(e) reconstructing a frame image representation from the echo signals of each group.

11. A cine magnetic resonance imaging method in which a positive portion of k-space is segmented into n segments, and a negative portion of k-space is segmented into a corresponding n segments, the first segment of both positive and negative k-space containing views with highest order frequency components, subsequent segments containing views with progressively lower order frequency components, and the nth positive and negative segments containing views with central-most, lowest order frequency components, the method comprising:

(a) monitoring cardiac cycles of a subject in a magnetic resonance imaging region;

(b) in coordination with each monitored cardiac cycle, generating a series of groups of consecutive echo sequences and receiving a corresponding plurality of groups of magnetic resonance echo signals, each echo signals corresponding to one view of k-space, the echo signals corresponding to views of the nth positive and negative segments of k-space being generated at a common, central position of each group;

(c) repeating step (b) with each of the groups at substantially the same time in each of a plurality of the monitored cardiac cycles;

(d) sorting the echo signals by group such that each group corresponds to a different time interval of each of the subject's cardiac cycles;

(e) reconstructing a frame image representation from the echo signals of each group.

12. The method as set forth in claim 11 wherein the views in k-space are numbered sequentially and wherein in each group, all of the views are one of even and odd numbered views.

13. The method as set forth in claim 11 wherein
the echo sequence generating step includes generating a motion sensitized echo sequence and a reference echo sequence and receiving a motion sensitized echo signal and a reference echo signal corresponding to each view of k-space;
in the sorting step, the reference and motion sensitized echo signals corresponding to each frame are separated;
in the reconstructing step, the motion sensitized and reference echo signals of each group are reconstructed into separate reference and motion sensitized frame images; and
further including subtracting the reference and motion sensitized frame images corresponding to the same group to create a flow image, whereby a plurality of flow images each corresponding to one of the time intervals of the subject's cardiac cycle are generated.

14. A cine magnetic resonance imaging method comprising:
(a) monitoring cardiac cycles of a subject in a magnetic resonance imaging region;
(b) in coordination with each monitored cardiac cycle, generating a series of groups of consecutive echo sequences and receiving a corresponding plurality of groups of magnetic resonance echo signals, each echo signal corresponding to one view of k-space in each group, a positive portion of k-space being segmented into n segments, a negative portion of k-space being segmented into a corresponding n segments, the first segment of both positive and negative k-space containing views with highest order frequency components, subsequent segments containing views with progressively lower order frequency components, and the nth positive and negative segments containing views with central-most, lowest order frequency components, adjacent pairs of echo sequences generate a motion sensitized echo signal and a reference echo signal corresponding to the same view;
(c) repeating step (b) with each of the groups at substantially the same time in each of a plurality of the monitored cardiac cycles;
(d) sorting the echo signals by group and by motion sensitized and reference signals within each group;
(e) reconstructing a motion sensitized frame image and a reference frame image from the echo signals of each group;
(f) subtracting the reference and motion sensitized frame images corresponding to the same group to create a flow image, whereby a plurality of flow images each corresponding to a plurality of different times within the subject's cardiac cycle are produced.

15. A cine magnetic resonance imaging method in which a positive portion of k-space is segmented into n segments, a negative portion of k-space is segmented into a corresponding n segments, the first segment of both positive and negative k-space containing views with highest order frequency components, subsequent segments containing views with progressively lower order frequency components, and the nth positive and negative segments containing views with central-most, lowest order frequency components, the method comprising:

(a) monitoring cardiac cycles of a subject in a magnetic resonance imaging region;
(b) in coordination with each monitored cardiac cycle, generating a series of groups of consecutive echo sequences and receiving a corresponding plurality of groups of magnetic resonance echo signals, each echo signal corresponding to one view of k-space in each group, adjacent pairs of echo sequences generate a motion sensitized echo signal and a reference echo signal corresponding to the same view in each group, echo signals corresponding to views from the nth positive and negative segments of k-space are generated most central within each group and echo signals corresponding to views from the first and second segmentations of k-space are at the ends of each group, whereby the central views are collected in the middle of each time interval of the subject's cardiac cycle;
(c) repeating step (b) with each of the groups at substantially the same time in each of a plurality of the monitored cardiac cycles;
(d) sorting the echo signals by group and by motion sensitized and reference signals within each group;
(e) reconstructing a motion sensitized frame image and a reference frame image from the echo signals of each group;
(f) subtracting the reference and motion sensitized frame images corresponding to the same group to create a flow image, whereby a plurality of flow images each corresponding to one of the subject's cardiac cycle time intervals are produced.

16. A cine magnetic resonance imaging method in which a positive portion of k-space is segmented into n segments and a negative portion of k-space is segmented into a corresponding n segments, the method comprising:
(a) monitoring cardiac cycles of a subject in a magnetic resonance imaging region;
(b) in coordination with each monitored cardiac cycle, generating a series of groups of consecutive echo sequences and receiving a corresponding plurality of groups of magnetic resonance echo signals, each echo signal corresponding to one view of k-space in each group, the views in k-space being numbered sequentially, adjacent pairs of echo sequences generate a motion sensitized echo signal and a reference echo signal corresponding to the same view in each group, all of the views being one of even and odd numbered views;
(c) repeating step (b) with each of the groups at substantially the same time in each of a plurality of the monitored cardiac cycles;
(d) sorting the echo signals by group and by motion sensitized and reference signals within each group;
(e) reconstructing a motion sensitized frame image and a reference frame image from the echo signals of each group;
(f) subtracting the reference and motion sensitized frame images corresponding to the same group to create a flow image.

17. A cine magnetic resonance imaging method comprising:
(a) monitoring cardiac cycles of a subject in a magnetic imaging region;
(b) in coordination with each monitored cardiac cycle, generating a series of groups of consecutive echo sequences and receiving a corresponding plurality of groups of magnetic resonance echo signals, the echo sequences generating motion sensitized echo signals and reference echo signals corresponding to each of a plurality of differently phase encoded views;

(c) repeating step (b) with each of the groups at substantially the same time in each of a plurality of the monitored cardiac cycles;

(d) sorting the echo signals by group and by motion sensitized and reference signals within each group;

(e) reconstructing a motion sensitized frame image and a reference frame image from the echo signals of each group;

(f) subtracting the reference and motion sensitized frame images corresponding to the same group to create a flow image, whereby a plurality of flow images corresponding to a plurality of different times within the subject's cardiac cycle are produced.

18. A cine magnetic resonance imaging apparatus comprising:

(a) a cardiac monitoring means for monitoring cardiac cycles of a subject in a magnetic resonance imaging region;

(b) a magnetic resonance echo signal generating means for generating a series of groups of consecutive echo generating magnetic resonance sequences and receiving a corresponding plurality of groups of magnetic resonance echo signals, in coordination with each of a plurality of monitored cardiac cycles, each echo signal corresponding to one view of k-space, a positive portion of k-space being segmented into n segments and a negative portion of k-space being segmented into a corresponding n segments, the first segment of both positive and negative k-space containing views with highest order frequency components, subsequent segments containing views with progressively lower order frequency components, and the nth positive and negative segments containing views with central-most, lowest order frequency components, all of the views of each group being from one of the positive k-space portion and the negative k-space portion, each of the groups of echo signals are received at substantially the same time in each of the plurality of the monitored cardiac cycles;

(c) a sorting means for sorting the echo signals by group such that each group corresponds to a different time interval of the subject's cardiac cycle;

(d) an image reconstruction means for reconstructing a frame image representation from the echo signals of each group.

19. A cine magnetic resonance imaging apparatus in which a positive portion of k-space is segmented into n segments, and a negative portion of k-space is segmented into a corresponding n segments, the first segment of both positive and negative k-space containing views with highest order frequency components, subsequent segments containing views with progressively lower order frequency components, and the nth positive and negative segments containing views with central-most, lowest order frequency components, the apparatus comprising:

(a) a cardiac monitoring means for monitoring cardiac cycles of a subject in a magnetic resonance imaging region;

(b) a magnetic resonance echo signal generating means for generating a series of groups of consecutive echo generating sequences and receiving a corresponding plurality of groups of magnetic resonance echo signals, each echo signal corresponding to one view of k-space, the echo signals corresponding to views of the nth segments of k-space being generated at a common, central position of each group, such that each of the groups of echo signals are received at substantially the same time in each of a plurality of the monitored cardiac cycles;

(c) a sorting means for sorting the echo signals by group such that each group corresponds to a different time interval of the subject's cardiac cycle;

(d) an image reconstruction means for reconstructing a frame image representation from the echo signals of each group.

20. A cine magnetic resonance imaging apparatus comprising:

(a) a cardiac monitoring means for monitoring cardiac cycles of a subject in a magnetic resonance imaging region;

(b) a means for generating a series of groups of consecutive echo generating sequences and receiving a corresponding plurality of groups of magnetic resonance echo signals in coordination with each monitored cardiac cycle, each echo signal corresponding to a one view of k-space such that in each group, adjacent pairs of echo sequences generate a motion sensitized echo signal and a reference echo signal corresponding to the same view, each of the groups being generated at substantially the same time in each of a plurality of the monitored cardiac cycles;

(c) a means for sorting the echo signals by group and by motion sensitized and reference signals within each group;

(d) a means for reconstructing a motion sensitized frame image and a reference frame image from the echo signals of each group;

(e) a means for subtracting the reference and motion sensitized frame images corresponding to the same group to create a flow image.

* * * * *